United States Patent [19]
Payrat et al.

[11] Patent Number: 5,906,915
[45] Date of Patent: *May 25, 1999

[54] METHOD FOR STORING RED CELLS USING REDUCED CITRATE ANTICOAGULANT AND A SOLUTION CONTAINING SODIUM, CITRATE, PHOSPHATE, ADENINE AND MANNITOL

[75] Inventors: Jean-Marc Payrat, Nivelles, Belgium; Claes F. Hogman, Uppsala, Sweden; Jack DeBrauwere, Halle; Jean Marie Mathias, Lillois, both of Belgium

[73] Assignee: Baxter International Inc., Deerfield, Ill.

[*] Notice: This patent issued on a continued prosecution application filed under 37 CFR 1.53(d), and is subject to the twenty year patent term provisions of 35 U.S.C. 154(a)(2).

[21] Appl. No.: 08/742,279

[22] Filed: Oct. 31, 1996

Related U.S. Application Data

[63] Continuation of application No. 08/491,099, Jun. 16, 1995, abandoned, which is a continuation of application No. 08/216,734, Mar. 22, 1994, abandoned, which is a division of application No. 07/610,478, Nov. 7, 1990, abandoned.

[51] Int. Cl.$^6$ .......................... A61K 35/18; A61K 35/14
[52] U.S. Cl. ............................................. 435/2; 424/93.75
[58] Field of Search ............................... 435/2; 424/93.75

[56] References Cited

U.S. PATENT DOCUMENTS

| | | | |
|---|---|---|---|
| Re. 32,874 | 2/1989 | Rock et al. | 424/101 |
| 4,082,509 | 4/1978 | Talcott | 21/58 |
| 4,222,379 | 9/1980 | Smith | 128/214 |
| 4,267,269 | 5/1981 | Grode et al. | 435/2 |
| 4,356,172 | 10/1982 | Nakao et al. | 424/101 |
| 4,572,899 | 2/1986 | Walker et al. | 436/18 |
| 4,585,735 | 4/1986 | Meryman et al. | 435/2 |
| 4,608,178 | 8/1986 | Johansson et al. | 210/744 |
| 4,675,185 | 6/1987 | Kandler et al. | 424/101 |
| 4,695,460 | 9/1987 | Holme | 424/101 |
| 4,704,352 | 11/1987 | Miripol et al. | 435/2 |
| 4,769,318 | 9/1988 | Hamasaki et al. | |
| 4,812,310 | 3/1989 | Sato et al. | 424/101 |
| 4,828,976 | 5/1989 | Murphy | 435/2 |
| 4,838,861 | 6/1989 | Sharp | 604/6 |
| 4,850,993 | 7/1989 | Champion et al. | 604/408 |
| 4,880,786 | 11/1989 | Sasakawa et al. | |
| 4,889,943 | 12/1989 | Kawamura et al. | |
| 4,892,537 | 1/1990 | Carmen et al. | 604/408 |
| 4,902,287 | 2/1990 | Carmen et al. | 604/416 |
| 4,961,928 | 10/1990 | Holme et al. | |
| 4,969,882 | 11/1990 | Carmen et al. | 604/410 |
| 4,994,056 | 2/1991 | Ikeda | 604/410 |
| 4,994,057 | 2/1991 | Carmen et al. | 604/416 |
| 4,997,083 | 3/1991 | Loretti et al. | 206/219 |
| 5,019,432 | 5/1991 | Kawamura et al. | 428/35.4 |
| 5,079,002 | 1/1992 | Nagai et al. | 424/400 |
| 5,248,506 | 9/1993 | Holme et al. | |
| 5,250,303 | 10/1993 | Meryman et al. | 424/533 |
| 5,494,590 | 2/1996 | Smith et al. | 210/782 |

FOREIGN PATENT DOCUMENTS

| | | |
|---|---|---|
| 0 099 315 | 2/1984 | European Pat. Off. . |
| 100 419 | 2/1984 | European Pat. Off. . |
| 0 044 864 B1 | 6/1985 | European Pat. Off. . |
| 0 301 250 | 6/1988 | European Pat. Off. . |
| 0 313 808 | 9/1988 | European Pat. Off. . |
| 0 142 339 B1 | 4/1989 | European Pat. Off. . |
| 108 588 | 6/1989 | European Pat. Off. . |
| 0 152 719 | 12/1981 | German Dem. Rep. . |
| 37 22 984A1 | 1/1989 | Germany . |
| 1106826 | 4/1989 | Japan . |
| WO81/02239 | 8/1981 | WIPO . |
| WO86/00809 | 2/1986 | WIPO . |
| WO88/1871 | 3/1988 | WIPO . |
| WO91/04659 | 4/1991 | WIPO . |
| WO 98/09660 | 3/1998 | WIPO . |

OTHER PUBLICATIONS

Rock G et al, NEJMED 311:310–313 (1984).
Asakuta et al., "pH dependency of 2,3–diphosphogylcerate content in red blood cells", *Clin. Chim. Acta*, vol. 14, 1966, pp. 840–841.
Funder et al., "Chloride and Hydrogen Ion Distribution between Human Red Cells and Plasma", *Acta Physiol. Scand.*, vol. 68, 1966, pp. 234–245.
LaCelle et al., "The Passive Permeability of the Red Blood Cells to Cations", *The Journal of General Physiology*, vol. 50, 1966, pp. 171–188.
Tsuboi, "Regulation of Erythrocyte Glycolysis Membrane–Mediated Activation Induced in Low–Electrolyte Medium", *Biochimica et Biophysica Acta*, vol. 352, 1974, pp. 307–320.
Tsuda et al., "Intracellular pH of Red Cells Stored in Acid Citrate Dextrose Medium", *Specialia, Experientia 28/12*, 1972, pp. 1481–1482.
Bessis, "Red Cell Shapes. An Illustrated Classification and Its Rationale", *Nouvelle Revue Française d'Hématologie*, vol. 12, No. 6, 1972, pp. 721–746.
Beutler et al., "Depletion and Regeneration of 2,3–diphosphoglyceric Acid in Stored Red Blood Cells", *Transfusion*, vol. 9, No. 3, 1969, pp. 109–113.

(List continued on next page.)

*Primary Examiner*—Sandra E. Saucier
*Attorney, Agent, or Firm*—Robert M. Barrett; Denise M. Serewicz; Bradford R. L. Price

[57] ABSTRACT

The present invention provides an improved aqueous solution for suspending and storing red blood cells. The solution includes sodium citrate, a combination of sodium biphosphate and sodium phosphate dibasic, adenine, and mannitol. The solution is formulated at a low osmolarity and has a physiological pH of approximately 7.4. The solution simultaneously maintains stored red cells ATP and 2,3-BPG. Also disclosed is a method for storing red blood cells comprising adding an anticoagulant with a reduced citrate concentration compared to a CPD solution comprising 26.3 g/l, sodium citrate and 3.28 g/l citric acid hydrous to whole blood, separating the red cells and adding a storage solution comprising sodium citrate, sodium diphosphate, sodium phosphate dibasic, adenine and mannitol.

11 Claims, 4 Drawing Sheets

OTHER PUBLICATIONS

Wood et al, "Storage of Erythorcytes in Artificial Media", *Transfusion*, vol. 11, No. 3, 1971, pp. 123–133.

Dern et al, "Studies on the preservation of human blood. II. The relationship of erythrocyte adenosine triphosphate levels and other in vitro measures to red cell storageability", *J. Lab. & Clin. Med.*, vol. 69, No. 6, 1967, pp. 968–978.

Matsuyama et al., "Lack of success with a combination of alanine and phosphoenolpyruvate as an additive for liquid storage of red cells at 4° C.", *Transfusion*, vol. 30, No. 4, 1990, pp. 339–343.

Högman et al., "Red Cell Suspensions in SAGM Medium", *Vox Sang*, vol. 45, 1983, pp. 217–223.

Moore et al., "Ascorbate–2–phosphate in red cell preservation: Clinical trials and active components", *Transfusion*, vol. 28, No. 3, 1988, pp. 221–225.

Vora et al., "The effect of additives on red cell 2,3 diphosphogylcerate levels in CPDA preservatives", *Transfusion*, vol. 219, No. 3, 1989, pp. 226–229.

Harmening et al, "The Use of Ion–Exchange Resins as a Blood Preservation System", *Transfusion*, vol. 19, No. 6, 1979, pp. 675–681.

Högman et al., "The Bottom and Top System: A New Technique for Blood Component Preparation and Storage", *Vox Sang*, vol. 55, 1988, pp. 211–217.

Moroff et al., "Proposed standardization of methods for determining the 24–hour survival of stored red cells", *Transfusion*, vol. 24, No. 2, 1984, pp. 109–114.

Griffin, B. et al.: "Studies on the Procurement of Blood Coagulation Factor VIII," *Vox Sang*. 55:9–13 (1988).

Matsuyama et al.: "Lack of Success with a Combination of Alanine and Phosphoenolpyruvate as an Additive for Liquid Storage of Red Cells at 4° C.," *Transfusion*, vol. 30, No. 4, 1990, pp. 339–343.

Meryman, H.T.: "Extended Storage of Washed Red Cells at 4° C.," Abstract–14th International Symposium on Blood Transfusion. Oct. 11–13, 1989.

Meryman, H.T. et al: "Prolonged Storage of Red Cells at 4° C.," *Transfusion*, vol. 26, No. 6, 1986, pp. 500–505.

Messeter et al.: "CPD–Adenine as a Blood Perservative—Studies in vitro and in vivo," *Chemical Abstracts*, vol. 87, No. 13, 1977, # 99582x.

Mezy et al.: "Study and Use of the ACD–Sdenine–Guanosine Blood Stabiliser," *Chemical Abstracts*, vol. 89, No. 19. 1978, Abstract # 16084w.

Mishler, J.M. et al.: "Whole Blood Storage in Citrate and Phosphate Solutions Containing Half–Strength Trisodium Citrate—Cellular and Biochemical Studies," *The Journal of Pathology*, vol. 124, No. 3, pp. 125–139 (1978).

Napier, J.A.F. et al.: "What is the 'Optimum' Optimal Additive Solution?" *Vox Sang*. 49:315–218 (1985).

Prowse, C. et al.: "Studies on the Procurement of Blood Coagulation Factor VIII in vitro Studies on Blood Components Prepared in Half–Strength Citrate Anticoagulant," *Vox Sang*. 52:257–264 (1987).

Robertson et al: "Macroaggregate Formation in Optimal Additive Red Cells," *Vox Sang*. 49:259–266 (1985).

Strauss et al.: "SAG–Sucrose Medium for Red Blood Cell Preservation," in *Chemical Abstracts*, vol. 106, No. 17, 1987, Abstract # 136009Z.

Valeri et al.: "Viability and Function of Red Blood Cell Concentrates Stored at 4° C. for 35 Days in CPDA–1, CPDA–2, or CPDA–3," *Transfusion*, vol. 22, No. 3, 1982, pp. 210–216.

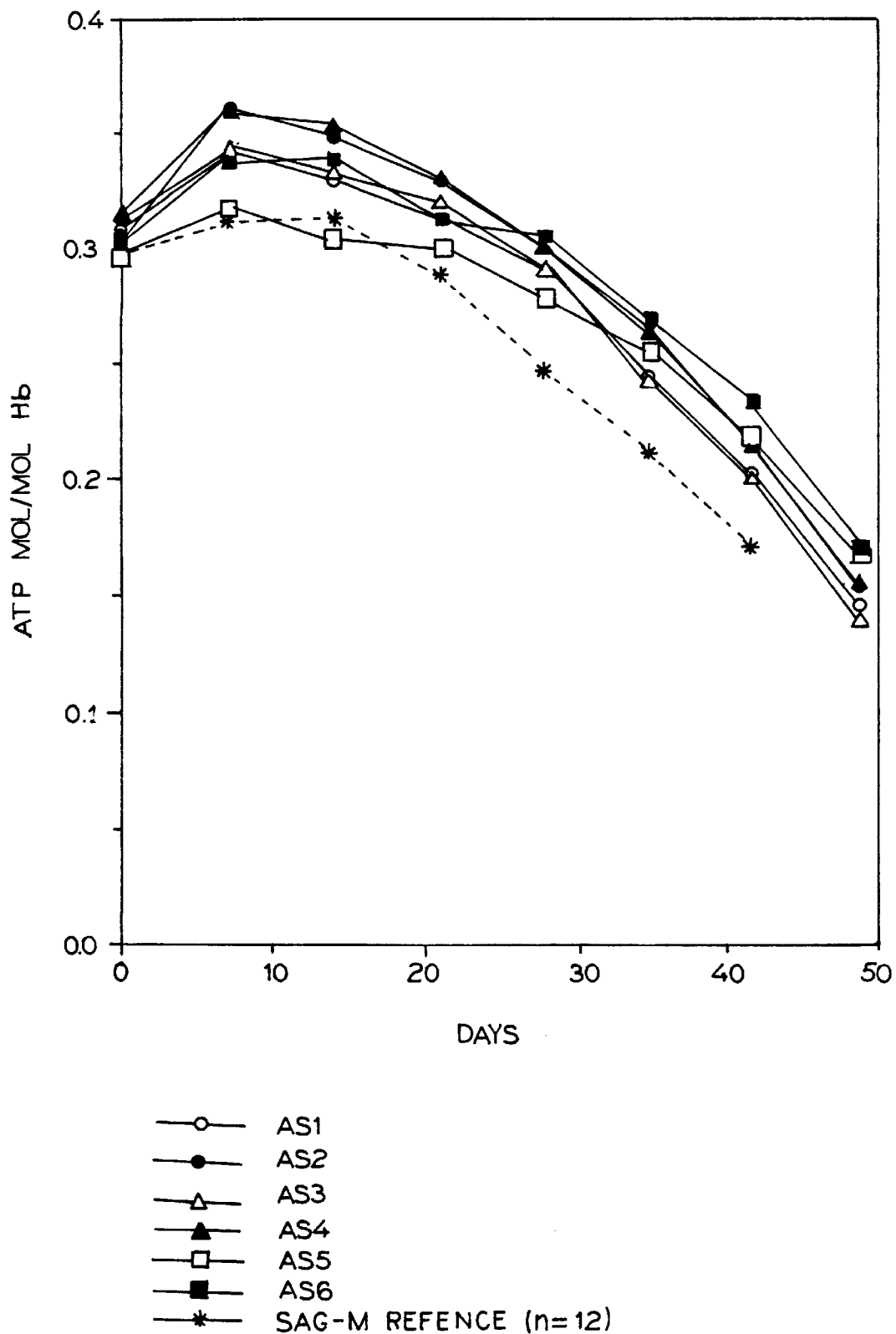

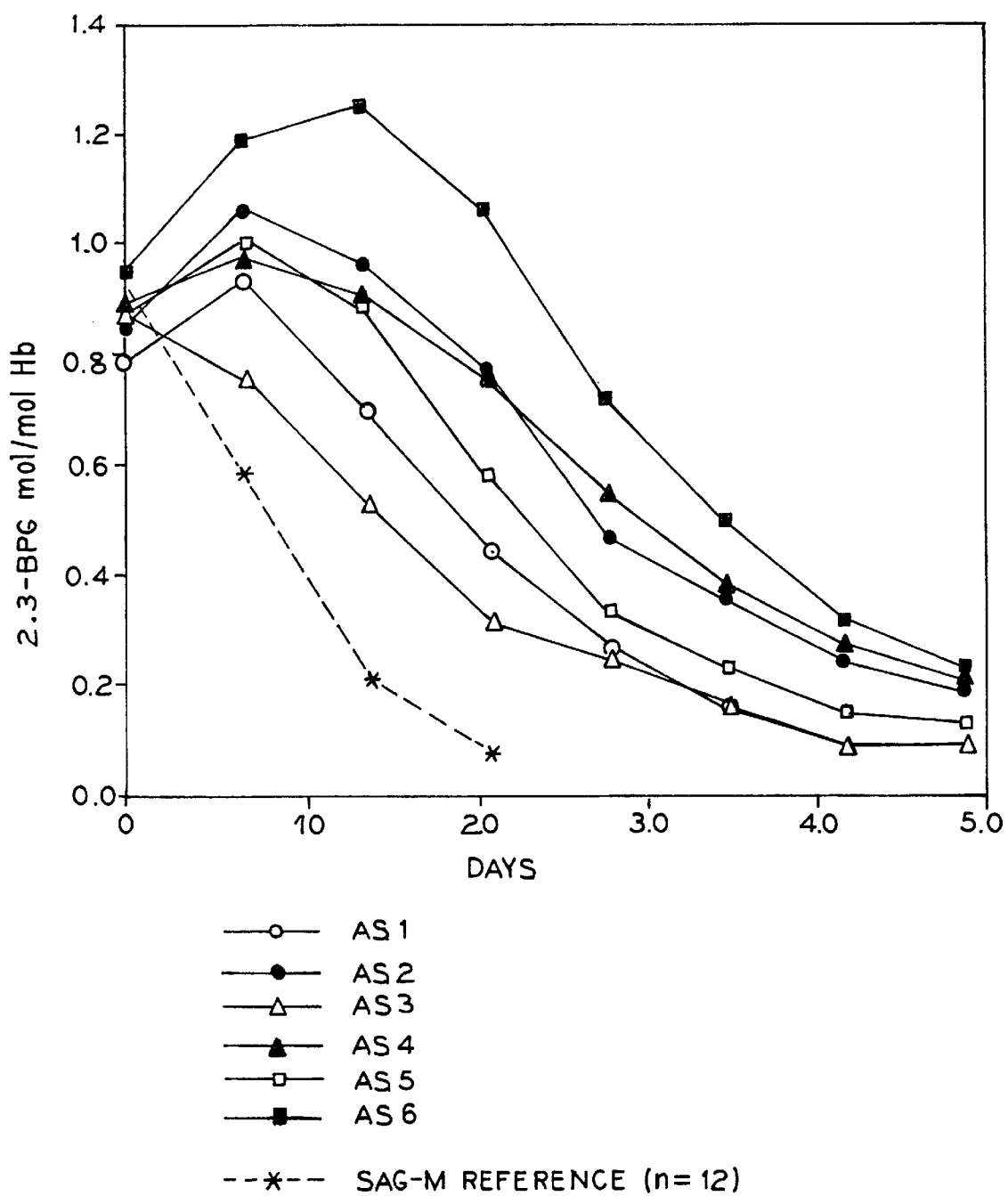

METHOD FOR STORING RED CELLS USING REDUCED CITRATE ANTICOAGULANT AND A SOLUTION CONTAINING SODIUM, CITRATE, PHOSPHATE, ADENINE AND MANNITOL

This application is a continuation of Ser. No. 08/491,099, filed Jun. 16, 1995, now abandoned, which is a continuation of Ser. No. 08/216,734 filed Mar. 22, 1994, now abandoned, which is a divisional of Ser. No. 07/610,478 filed Nov. 7, 1990 now abandoned.

BACKGROUND OF THE INVENTION

The present invention relates generally to the storage of blood cell components. More specifically, the present invention relates to the storage of the red blood cell component of blood.

It is known to centrifuge collected blood to remove plasma and the buffy-coat layer. The residue is a mass of red cells that is substantially separated from the plasma referred to as "packed red cells." The separation of the red cells from the plasma is desirable for a number of reasons. By separating the red cells, it is possible to collect the plasma and use the plasma for separate therapeutic uses.

Additionally, it is desirable in many disease states to administer red blood cells in a purified or semipurified form, thereby avoiding to transfer to the recipient such constituents of blood as plasma and white cells, when these are unsuitable.

Accordingly, it is known to store packed red cells separately and apart from at least a substantial portion of plasma. These red cells are later administered to a patient during major surgery and the like.

Although it is desirable to separately store and utilize the red cell component of whole blood, it was discovered that, unless special precautions are taken, packed red cells do not survive as well as red cells that are stored in the presence of an increased amount of plasma. Accordingly, to promote the long term storage of packed red cells, it has been suggested to admix packed red cells with at least a small amount of blood plasma.

It is known to store packed red cells in a 100 ml of a protein-poor solution containing for each unit of packed red cells, 877 mg of sodium chloride, 16.9 mg of adenine, and 900 mg of glucose (SAG) to increase the storage life of the red cells. See, Hogman et al, New England Journal of Medicine, Dec. 21, 1978; 229 (25); 1377–82.

It has also been suggested to use mannitol as a reagent to improve the viability of stored blood cells and create a storage solution. See, U.S. Pat. No. 4,082,509. The patent discloses a storage solution which includes both glucose (in an amount of 990 mg/ml) and mannitol (in an amount of 500 mg/ml). The solution provides an improved viability of the packed red cells stored in contact therewith.

European Published Patent No. 0 044 864 discloses a storage solution that provides improved storage time. Pursuant to the solution disclosed, the concentration of glucose (or fructose) is increased and mannitol is added to a conventional SAG solution. In an embodiment, an aqueous red blood cell storage solution is provided that contains per 100 ml of solution, substantially from 1500 to 2500 mg of sugar comprising glucose and/or fructose; from 500 to 1500 mg of mannitol; from 20 to 30 mg of adenine; and from 500 to 1000 mg of sodium chloride.

One difficulty that is encountered with storage solutions is the sterilization of the solutions. Glucose is known to degrade under autoclaving (heat) sterilization conditions unless it is maintained in an acidic medium. If glucose is not in an acidic medium, when heated, glucose will carmelize.

In collecting blood, specifically red cells, it is known to add to the whole blood collected from the donor an anticoagulant. The anticoagulant typically includes citrate. After the anticoagulant is added to the whole blood, the blood can be separated into components, including plasma and red blood cells. An example of an anticoagulant is citrate phosphate dextrose (CPD). During the separation process of the whole blood, typically much of the citrate separates with the plasma, leaving the red blood cells with lower citrate levels when they are then mixed with a storage solution.

It is known to include in the anticoagulant a surplus of citrate in order to obtain good binding of ionized calcium which otherwise may initiate plasma coagulation at blood collection or blood storage. However, a disadvantage with this procedure is poor stability of Factor VIII and reduced yield of this factor in subsequent blood component preparation.

It is known that reduction of the concentration of citrate in the anticoagulant improves the stability of Factor VIII, provided conditions during collection are optimal. This is a way to improve the yield of Factor VIII in plasma, when separation of the blood into components has to be carried out after a delay of several hours. Reduction of citrate in the anticoagulant has the additional advantage, when the red cells are stored in an additive solution based on citrate, that the citrate load in a recipient of massive volumes of both red cells and plasma will not be disturbingly high.

There is therefore a need for an improved red blood cell storage solution.

SUMMARY OF THE INVENTION

The present invention provides an improved aqueous solution for suspending and storing red blood cells. The solution includes sodium citrate, a combination of sodium biphosphate and sodium phosphate dibasic, adenine, and mannitol.

Preferably, the solution has been adjusted to a physiological pH of about 7.4.

Preferably, the solution is formulated at a low osmolarity. To this end, the solution preferably does not include sodium chloride.

In an embodiment, the solution can be utilized with an anticoagulant solution having a reduced citrate concentration. For example, the anticoagulant solution can include, approximately 50% less citrate concentration than is typically utilized in a CPD anticoagulant solution.

In a preferred embodiment, the present invention provides an aqueous red blood cell storage solution comprising sodium citrate, sodium biphosphate, sodium phosphate dibasic, adenine, and mannitol. The solution has a pH of approximately 7.4 and an osmolarity of less than 300 mOsm/l. In an embodiment, the aqueous red blood cell storage solution includes guanosine.

In an embodiment, the present invention provides an aqueous red blood cell storage solution that is added to a plasma depleted collection of red blood cells, comprising in millimolar concentration (mmol/l): approximately 20 mmol/l to about 140 mmol/l of at least one sugar chosen from the group consisting of dextrose and fructose; approximately 1 mmol/l to about 2.2 mmol/l of adenine; approximately 20 mmol/l to about 110 mmol/l mannitol; approximately 2.2 mmol/l to about 90 mmol/l sodium citrate;

approximately 1 mmol/l to about 10 mmol/l sodium biphosphate; approximately 5 mmol/l to about 25 mmol/l sodium phosphate dibasic and approximately 0 to about 2 mmol/l guanosine; per 100 ml of solution.

Preferably a two part aqueous red blood cell storage solution is provided. The solution includes a first part including sodium citrate, sodium biphosphate, sodium phosphate dibasic, adenine, and mannitol, and no sodium chloride. A second part including a sugar chosen from the group consisting of dextrose and fructose.

The present invention also provides a method of storing red blood cells comprising the step of combining a plasma depleted collection of red blood cells with an aqueous storage solution comprising sodium citrate, sodium biphosphate, sodium phosphate dibasic, adenine, and mannitol, and having a pH of approximately 7.4 and an osmolarity of less than 300 mOsm/l. In an embodiment, an anticoagulant having a reduced citrate concentration is utilized.

Additional features and advantages of the present invention are described in, and will be apparent from, the detailed description of the presently preferred embodiments and from the drawings.

BRIEF DESCRIPTION OF THE DRAWINGS

FIG. 3 illustrates graphically ATP mol/mol Hb versus days for red cells stored in examples of the solution of the present invention and in a SAG-M reference solution.

FIG. 4 illustrates graphically 2,3-BPG mol/mol Hb versus days for examples of the solution of the present invention and a SAG-M reference solution.

DETAILED DESCRIPTION OF THE PRESENTLY PREFERRED EMBODIMENTS

The present invention provides an aqueous solution for suspending and storing red cells. The solution includes sodium citrate, a combination of sodium biphosphate and sodium phosphate dibasic, adenine, and mannitol. Preferably, the solution has been adjusted to a physiological pH of about 7.4. The solution is stable on steam sterilization in PVC containers. The solution is also formulated at a low osmolarity. Accordingly, the solution preferably does not include sodium chloride.

Because dextrose, or fructose, is necessary for the maintenance of red cell metabolism, dextrose or fructose is preferably provided to the collection of red blood cells. In an embodiment of the invention, the dextrose, or fructose, is provided separately from the basic formulation in the form of an acid concentrate solution.

Figure 1:
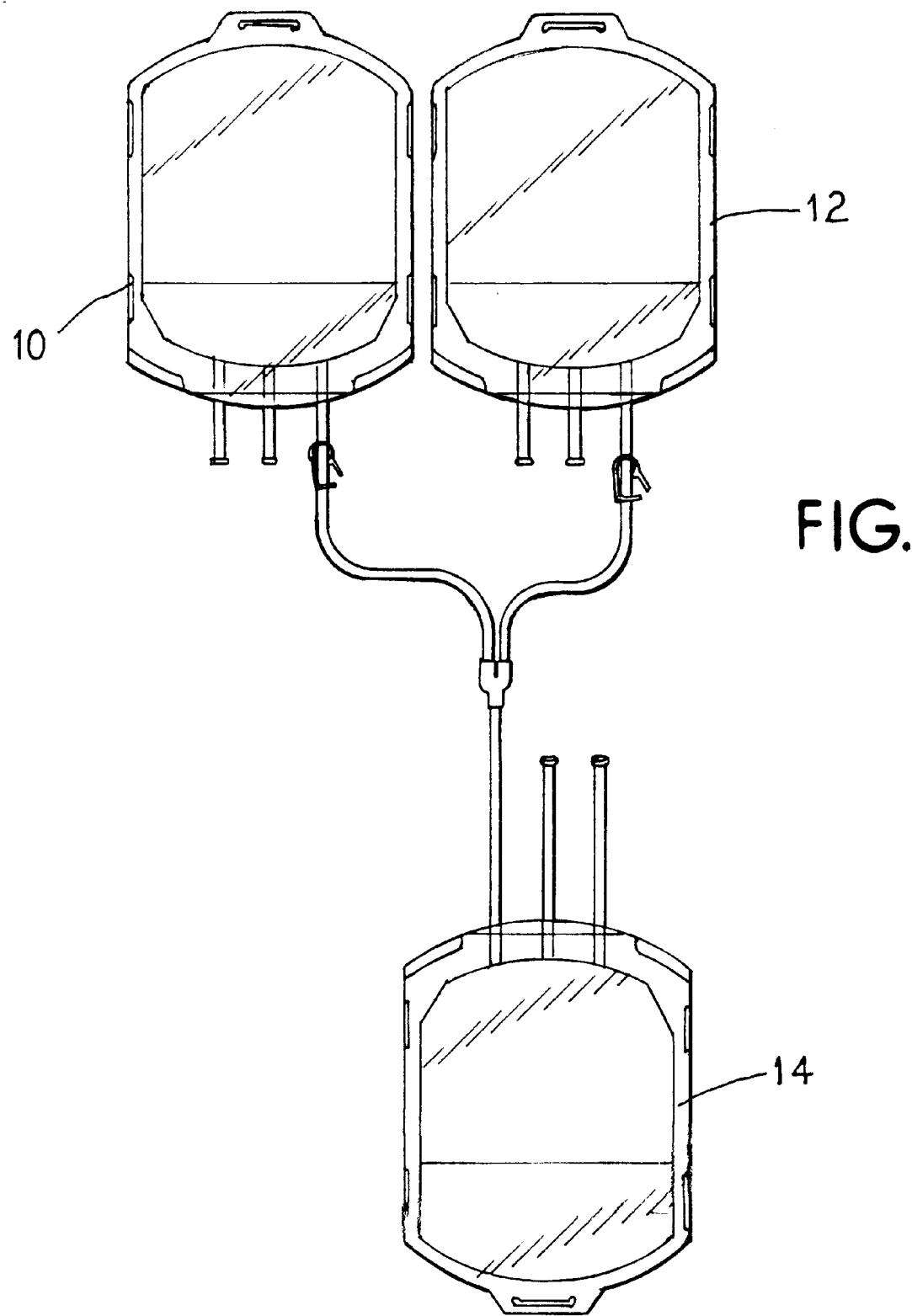
FIG. 1 illustrates a perspective view of a first, second and third container for housing, respectively, a sugar medium, the storage solution, and plasma depleted red blood cells.

For example, the basic formulation can be contained in a first container or compartment, and mixed with dextrose which is in a separate container or compartment. After the components are mixed they can then be added to the red cells obtained from whole blood. To this end, as illustrated in the embodiment of the invention set forth in FIG. 1, two containers 10 and 12 are provided. The sugar component can be housed in the first container 10 and the solution in the second container 12. A further container 14, that houses the red blood cells is also provided.

Alternatively, a blood bag system such as that disclosed in U.S. Pat. No. 4,608,178 can be used, the disclosure of which is incorporated by reference herein.

By maintaining the sugar component separate from the remaining solution, pursuant to the present invention, the solution can be maintained at a physiological pH of approximately 7.4. On the other hand, the sugar medium can be maintained at an acidic pH. Although the sugar will be maintained at an acidic pH, the solution has sufficient buffer capacity so that when the sugar is added to the solution, and then the red blood cells, the pH remains fairly constant at around 7.4. Additionally, by so separately the component, the solution and sugar can be maintained in PVC containers reduceing costs.

Typically, when the red cells obtained from whole blood are collected they are collected with an anticoagulant solution. An example of such a solution is citrate phosphate dextrose formulation. In an embodiment, of the solution of the present invention, the red blood cell storage solution is used with an anticoagulant having a reduced citrate level. For example, a CPD solution that includes only 50% of the typical citrate concentration of a CPD solution.

Examples of a CPD and a CPD 50% citrate are as follows (in grams per liter):

|  | CPD | 50% CITRATE |
|---|---|---|
| $Sodium_3$ Citrate Dihydrate | 26.30 | 13.15 |
| Citric Acid Hydrous | 3.29 | 1.64 |
| Dextrose Monohydrate | 25.50 | 25.50 |
| Sodium Biphosphate Monohydrate | 2.22 | 2.22 |

The solution of the present invention, including dextrose, when added to red cells enables the cells to be stored for at least 42 days. The solution has been found to have the equivalent of efficacy for ATP maintenance and limitation of hemolysis to that of currently used saline-adenine-glucose-mannitol (SAG-M) or a solution such as that set forth in European Patent No. 0 044 864, the disclosure of which is incorporated herein by reference.

In an embodiment, the solution that is used for the storage of red blood cells comprises in millimolar-concentration: approximately 20 to 140 mmol/l dextrose (and/or fructose); approximately 1 to about 2.2 mmol/l adenine; approximately 20 to about 110 mmol/l mannitol; approximately 2.2 to about 90 mmol/l sodium citrate; approximately 1 to about 10 mmol/l sodium biphosphate; approximately 5 to about 25 mmol/l sodium phosphate dibasic; and approximately 0 to about 2 mmol/l guanosine.

Preferably, 50 to about 200 ml of solution is used. Most preferably, 75 to about 150 ml of solution is used.

It has been found that the most preferable ranges are as follows for a 100 ml volume of solution in a millimolar concentration: approximately 30 to about 60 mmol/l dextrose and/or fructose; approximately 1.2 to about 1.7 mmol/l adenine; approximately 30 to about 50 mmol/l mannitol; approximately 4.5 to about 55 mmol/l sodium citrate; approximately 2 to about 5 mmol/l sodium biphosphate; approximately 8 to about 18 mmol/l sodium phosphate dibasic; and approximately 0 to about 1.5 mmol/l guanosine. Preferably, the sugar component is housed in a separate container or compartment at an acidic pH. The remaining constituents are then maintained at a pH of approximately 7.4.

The above solution provides a red cell storage solution with a low osmolarity. Preferably the osmolarity is less than 300 mOsm/l. It is believed that an osmolarity of less than 300 mOsm/l reduces the concentration of $H^+$ inside the red blood cells that are stored in the solution and better approximates the physiological $H^+$ concentration. Furthermore, the above solution can be utilized with a low citrate anticoagulant.

In an embodiment for use with a reduced citrate CPD anticoagulant, citric acid can be added to the solution. In an embodiment, in millimolar concentration, approximately 0.4 to about 15 mmol/l of citric acid is added. It has been found that the most preferable ranges for citric acid are 0.8 to about 9.5 mmol/l.

Although, preferably the sugar component is housed in a separate container, constituents that are not effected by an acidic environment can be housed with the sugar component. For example, mannitol, adenine, and sodium citrate.

By way of example, and not limitation, examples of the invention will now be given.

A series of six solutions were tested.

The concentration in the red cells of 2,3-BPG is related to oxygen delivery capacity of the cells. 2,3-BPG is generally poorly maintained in known solutions for red cell storage dropping to levels of about 5 to about 10 percent of the initial value within 14 to 21 days of refrigerated storage. As set forth in detail below, with the solution of the present invention, 2,3-BPG remains at about 80 to about 110 percent of initial concentration after 21 days and about 30 percent after 42 days.

was not adjusted but was naturally acidic (pH 5.8). The mixture of the two containers after steam sterilization resulted in a solution having a pH ranging from 7.41 to 7.46 depending on the formulations (see Table 1).

The test variables and experiments were as follows: a low (solutions 1, 3, 5) versus a high (solutions 2, 4, 6) phosphate level; and the effect of sodium gluconate (solutions 3, 4) or guanosine (solutions 5, 6).

Four series of six units of whole blood were drawn on a citrate formulation having a reduced citrate concentration, CPD 50% citrate. Plasma and the buffy coat layer were removed from centrifuged units. Each group of red cell concentration (RCC) were pulled together then subdivided into six containers containing each of the tested solutions (set forth above as 1–6).

Figure 2:
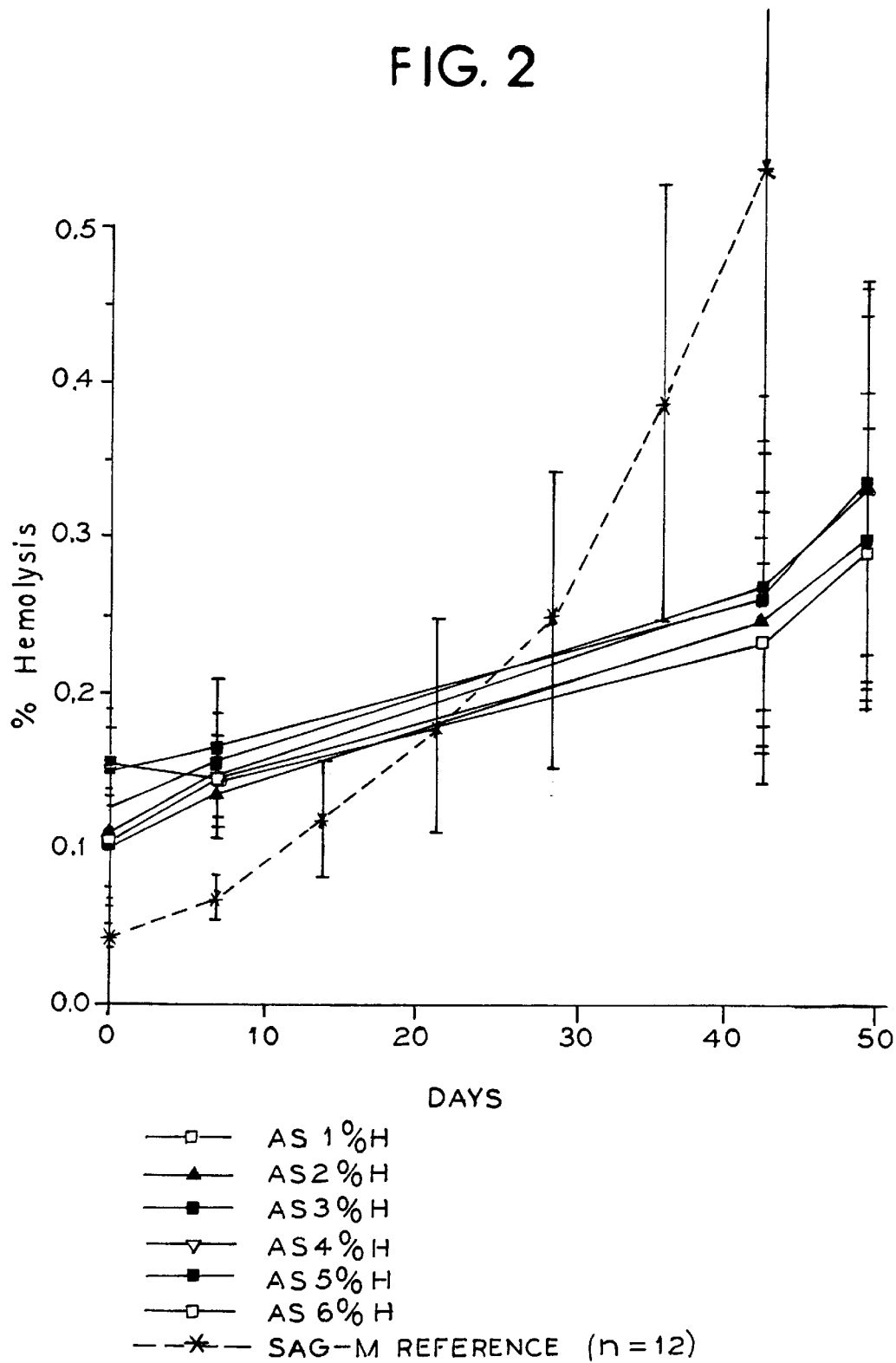
FIG. 2 illustrates graphically percent hemolysis versus days for red cells stored in examples of the solution of the present invention and in a SAG-M reference solution.

Suspended RCC were stored at ±4° C. for 50 days. Referring now to the Figures, the graphs illustrate the evolution of hemolysis, ATP, and 2,3-BPG, respectively, in the tested formulations (see FIGS. 2, 3 and 4). As a comparison, the evolution of the same parameters for SAG-M resuspended red cell storage in the same plastic containers and tested in the same laboratory is shown in broken lines in FIGS. 2, 3, and 4 (from Hogman, C. F. et al, *Storage of SAG-M Suspended Red Cells in a New Plastic Container: PVC Plasticized with Butyryl-n-Trihexyl-Citrate*, In Press, Transfusion). The SAG-M mixture was as follows in grams per liter: 9.00 dextrose monohydrate, 8.77 sodium chloride, 0.169 adenine, 5.25 mannitol, and an osmolality of 376.

TABLE 1

RED CELLS ADDITIVE SOLUTIONS

MILLIMOLAR CONCENTRATION (mmol/l) IN
SOLUTION A + B:100 ML

| TYPE | Sodium citrate $C_6H_5Na_3O_7 \cdot 2H_2O$ | Sodium bisphosphate $NaH_2PO_4 \cdot H_2O$ | Sodium phosphate dibasic $Na_2HPO_4 \cdot 2H_2O$ | Sodium gluconate $C_6H_{11}NaO_7$ |
|---|---|---|---|---|
| 1 | 25.0 | 2.34 | 9.64 | — |
| 2 | 25.0 | 3.91 | 16.09 | — |
| 3 | 25.0 | 2.34 | 9.64 | 25.0 |
| 4 | 25.0 | 3.91 | 16.09 | 25.0 |
| 5 | 25.0 | 2.34 | 9.64 | — |
| 6 | 25.0 | 3.91 | 16.09 | — |

| TYPE | Mannitol $C_6H_{14}O_6$ | Adenine $C_5H_5N_5$ | Guanosine $C_{10}H_{13}N_5O_5$ | Dextrose $C_6H_{12}O_6 \cdot H_2O$ | pH after ster. | Osmolality (mOsm/k9) after ster. |
|---|---|---|---|---|---|---|
| 1 | 40.0 | 1.5 | — | 45.4 | 7.46 | 193 |
| 2 | 40.0 | 1.5 | — | 45.4 | 7.44 | 209 |
| 3 | 40.0 | 1.5 | — | 45.4 | 7.42 | 238 |
| 4 | 40.0 | 1.5 | — | 45.4 | 7.41 | 252 |
| 5 | 40.0 | 1.5 | 1.2 | 45.4 | 7.46 | 193 |
| 6 | 40.0 | 1.5 | 1.2 | 45.4 | 7.44 | 215 |

Table 1, above, sets forth the detailed formulations expressed in millimolar concentration, mmol/l for 100 milliliter final volume of red cell additive solutions. Citrate, phosphate, mannitol, adenine, and some formulations with sodium gluconate or guanosine were sterilized in PVC containers and housed in an 80 ml volume (container A). Dextrose was sterilized separately in small capacity PVC containers filled with 20 milliliter solution (container B).

Physiological pH (approximately 7.4) was achieved in container A by using an adequate balance of sodium biphosphate and sodium phosphate dibasic. The pH of container B From these experiments, it was demonstrated that all six tested formulations limit hemolysis during RCC storage to very low levels (about 50% of SAG-M reference solution). ATP is at least as well maintained as in reference SAG-M solution. 2,3-BPG is far better maintained than in the SAG-M reference solution especially in high phosphate formulations. The presence of guanosine also seems beneficial to 2,3-BPG maintenance.

Although it is desirable to include a sufficient amount of dextrose in the solution to supply sufficient nutrients to the red cells for prolonged storage, it is possible to supply sufficient dextrose to the red cells by increasing the concentration of dextrose in the anticoagulant formula. Accordingly, the solution of the present invention can be utilized with no dextrose in the red cell additive solution by using a high dextrose anticoagulant formulation. For example, it is anticipated that if the dextrose in the CPD anticoagulant is increased by 100% then the additive solution can be used without the further addition of a sugar.

Preferably the solution includes no sodium chloride. However, in order to provide a slightly more physiological osmolarity, it is possible that a minimal amount of sodium chloride could be present in the solution.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A method for storing red blood cells comprising the steps of:

adding a citrate phosphate dextrose anticoagulant, that has a reduced level of citrate as compared to a typical citrate phosphate dextrose anticoagulant formulation, to collected whole blood, the typical citrate phosphate dextrose anticoagulant formulation containing 26.3 g/l of sodium citrate dihydrate and 3.28 g/l of citric acid hydrous, the anticoagulant having a sufficient level of dextrose to provide a nutrient supply to separated red blood cells;

separating the red blood cells from the whole blood; and adding to the separated red blood cells an aqueous storage solution comprising sodium citrate, sodium diphosphate, sodium phosphate dibasic, adenine, and mannitol, the aqueous storage solution including a sufficient amount of sodium diphosphate and sodium phosphate dibasic so as to maintain a 2,3 diphosphoglycerate concentration in the red cells stored at refrigeration temperatures to at least 80% of an initial concentration for at least 21 days.

2. The method of claim 1 wherein the pH of the storage solution is 7.4.

3. The method of claim 1 wherein the storage solution comprises:

approximately 1 mmol/l to about 2.2 mmol/l adenine;

approximately 20 mmol/l to about 110 mmol/l mannitol;

approximately 2.2 mmol/l to about 90 mmol/l sodium citrate;

3.91 mmol/l sodium biphosphate;

16.09 mmol/l sodium phosphate dibasic; and approximately 0 mmol/l to about 2 mmol/l guanosine.

4. The method of claim 1 wherein the storage solution further comprises citric acid.

5. The method of claim 1 wherein the aqueous storage solution has an osmolarity of less than 300 mOsm/l.

6. The method of claim 1 wherein the storage solution further comprises guanosine.

7. The method of claim 1 wherein the citrate level is less than or equal to 50% of the typical CPD anticoagulant.

8. A method of storing red blood cells comprising the steps of:

adding a citrate phosphate dextrose anticoagulant having a citrate level that is reduced as compared to a typical citrate phosphate dextrose anticoagulant to whole collected blood, the typical citrate phosphate dextrose anticoagulant comprising 26.3 g/l of sodium citrate dihydrate and 3.28 g/l of citric acid hydrous;

separating the red blood cells from the whole blood; and adding to the red blood cells an aqueous storage solution comprising sodium citrate, sodium diphosphate, sodium phosphate dibasic, adenine, and mannitol, the aqueous storage solution including a sufficient amount of sodium diphosphate and sodium phosphate dibasic such that a 2,3 diphosphoglycerate concentration in the red cells remains at about 80% to about 110% of an initial 2,3 diphosphoglycerate concentration if the red cells are stored, at refrigeration temperatures, for 21 days.

9. The method of claim 8 wherein the storage solution comprises:

approximately 20 mmol/l to about 140 mmol/l of at least one sugar chosen from the group consisting of dextrose and fructose;

approximately 1 mmol/l to about 2.2 mmol/l adenine;

approximately 20 mmol/l to about 110 mmol/l mannitol;

approximately 2.2 mmol/l to about 90 mmol/l sodium citrate;

3.91 mmol/l sodium biphosphate;

16.09 mmol/l sodium phosphate dibasic; and approximately 0 mmol/l to about 2 mmol/l guanosine.

10. The method of claim 8 wherein the amount of phosphate is approximately 20 mmol/l.

11. The method of claim 8 wherein the citrate level is less than or equal to 50% of the typical citrate phosphate dextrose anticoagulant.

* * * * *